United States Patent
Baldwin et al.

(10) Patent No.: US 6,443,963 B1
(45) Date of Patent: Sep. 3, 2002

(54) APPARATUS AND METHOD FOR REPAIRING OR REATTACHING SOFT TISSUE

(75) Inventors: Jeffrey P Baldwin, Phoenix, AZ (US); Robert E. Hunter, Aspen, CO (US); Laird L. Hatch, Cave Creek, AZ (US); Jenine S. Vinluan, Scottsdale, AZ (US)

(73) Assignee: Orthopaedic Biosystems, Ltd., Scottsdale, AZ (US)

( * ) Notice: Subject to any disclaimer, the term of this patent is extended or adjusted under 35 U.S.C. 154(b) by 0 days.

(21) Appl. No.: 09/626,071

(22) Filed: Jul. 26, 2000

(51) Int. Cl.⁷ ............................................. A61B 17/04

(52) U.S. Cl. .................... 606/148; 606/139; 606/146

(58) Field of Search ............................... 606/213, 219, 606/139, 14, 148

(56) References Cited

U.S. PATENT DOCUMENTS

| | | |
|---|---|---|
| 659,422 A | 10/1900 | Shidler |
| 1,635,066 A | 7/1927 | Wells |
| 2,065,659 A | 12/1936 | Cullen |
| 2,610,631 A | 9/1952 | Calicchio |
| 2,880,728 A | 4/1959 | Rights |
| 3,013,559 A | 12/1961 | Thomas |
| 3,103,666 A | 9/1963 | Bone |
| 3,349,772 A | 10/1967 | Rygg |
| 3,470,875 A | 10/1969 | Johnson |
| 3,638,653 A | 2/1972 | Berry |
| 3,699,969 A | 10/1972 | Allen |
| 3,840,017 A | 10/1974 | Violante |
| 3,842,840 A | 10/1974 | Schweizer |
| 3,871,379 A | 3/1975 | Clarke |
| 3,901,244 A | 8/1975 | Schweizer |
| 3,946,740 A | 3/1976 | Bassett |
| 4,164,225 A | 8/1979 | Johnson et al. |
| 4,224,947 A | 9/1980 | Fukuda |
| 4,493,323 A | 1/1985 | Albright et al. |
| 4,591,085 A | 5/1986 | Di Giovanni |
| 4,605,004 A | 8/1986 | Di Giovanni et al. |
| 4,606,344 A | 8/1986 | Di Giovanni |
| 4,606,345 A | 8/1986 | Dorband et al. |
| 4,607,636 A | 8/1986 | Kula et al. |
| 4,890,615 A | 1/1990 | Caspari ...................... 606/146 |
| 4,923,461 A | 5/1990 | Casari et al. |
| 4,935,027 A | 6/1990 | Yoon ........................... 606/146 |
| 4,957,498 A | 9/1990 | Caspari ...................... 606/146 |
| 5,078,730 A | 1/1992 | Li et al. |
| 5,100,418 A | 3/1992 | Yoon et al. |
| 5,152,763 A | 10/1992 | Johnson |

(List continued on next page.)

FOREIGN PATENT DOCUMENTS

| | | |
|---|---|---|
| DE | 3831398 | 3/1990 |
| EP | 0 241 240 | 10/1987 |
| FR | 1539593 | 9/1968 |
| WO | WO 91/02490 | 7/1991 |
| WO | WO 95/02363 | 1/1995 |
| WO | WO 96/27331 | 9/1996 |
| WO | WO 99/03402 | 1/1999 |
| WO | WO 99/12480 | 3/1999 |

Primary Examiner—Gary Jackson
(74) Attorney, Agent, or Firm—Fish & Richardson P.C.

(57) ABSTRACT

An apparatus and method for delivering or installing a surgical suture or suture-like implant into soft tissue, such as the meniscus of the knee, for example, for reattachment or repair of that tissue. The apparatus and method facilitate ease of placement of the suture or implant by the surgeon, protect surrounding tissue and nerves from damage during use, and permit suturing to occur through a single body portal. An injury to soft tissue, such as a tear in the meniscus of the knee joint or detachment of soft tissue from bone, is repaired through a single body portal by installing a surgical suture across the injury, tear, or detachment and passing that suture back through the body portal so that the suture can be joined and the injury, tear, or detachment can be reapproximated by the surgeon while working through the single body portal.

38 Claims, 10 Drawing Sheets

U.S. PATENT DOCUMENTS

| | | |
|---|---|---|
| 5,181,919 A | 1/1993 | Bergman et al. |
| 5,192,287 A | 3/1993 | Fournier et al. |
| 5,254,126 A | 10/1993 | Filipi |
| 5,269,783 A | 12/1993 | Sander |
| 5,306,280 A | 4/1994 | Bregen et al. |
| 5,334,198 A | 8/1994 | Hart et al. |
| 5,336,231 A | 8/1994 | Adair |
| 5,372,604 A | 12/1994 | Trott |
| 5,411,522 A | 5/1995 | Trott |
| 5,439,474 A | 8/1995 | Li |
| 5,442,472 A | 8/1995 | Li |
| 5,466,243 A | 11/1995 | Schmieding et al. |
| 5,500,001 A | 3/1996 | Trott |
| 5,501,683 A | 3/1996 | Trott |
| 5,527,322 A | 6/1996 | Klein et al. |
| 5,545,170 A | 8/1996 | Hart |
| 5,549,636 A | 8/1996 | Li |
| 5,562,683 A | 10/1996 | Chan |
| 5,562,687 A | 10/1996 | Chan |
| 5,569,269 A | 10/1996 | Hart et al. |
| 5,571,090 A | 11/1996 | Sherts |
| 5,618,304 A | 4/1997 | Hart et al. |
| 5,645,552 A | 7/1997 | Sherts |
| 5,658,299 A | 8/1997 | Hart |
| 5,665,096 A | 9/1997 | Yoon .................. 606/139 |
| 5,683,401 A | 11/1997 | Schmieding et al. |
| 5,792,152 A | 8/1998 | Klein et al. .................. 606/144 |
| 5,797,927 A | 8/1998 | Yoon |
| 5,814,054 A | 9/1998 | Kortenbach |
| 5,814,069 A | 9/1998 | Schulze et al. |
| 5,826,776 A | 10/1998 | Schulze et al. |
| 5,846,254 A | 12/1998 | Schulze et al. |
| 5,855,311 A | 1/1999 | Hamblin et al. |
| 5,895,395 A | 4/1999 | Yeung |
| 5,897,563 A | 4/1999 | Yoon et al. |
| 5,897,564 A | 4/1999 | Schulze et al. |
| 5,904,692 A | 5/1999 | Steckel et al. |
| 5,908,428 A | 6/1999 | Scirica |
| 5,928,252 A | 7/1999 | Steadman |
| 5,941,439 A | 8/1999 | Kammerer et al. |
| 5,993,466 A | 11/1999 | Yoon .................. 606/147 |
| 6,010,513 A | 1/2000 | Tormala |
| 6,039,753 A | 3/2000 | Meislin |
| 6,059,800 A | 5/2000 | Hart et al. .................. 606/144 |
| 6,071,289 A | 6/2000 | Stefanchik et al. |
| 6,074,395 A | 6/2000 | Trott et al. |
| 6,074,403 A | 6/2000 | Nord |
| 6,077,276 A | 6/2000 | Kontos .................. 606/144 |
| 6,086,601 A | 7/2000 | Yoon |

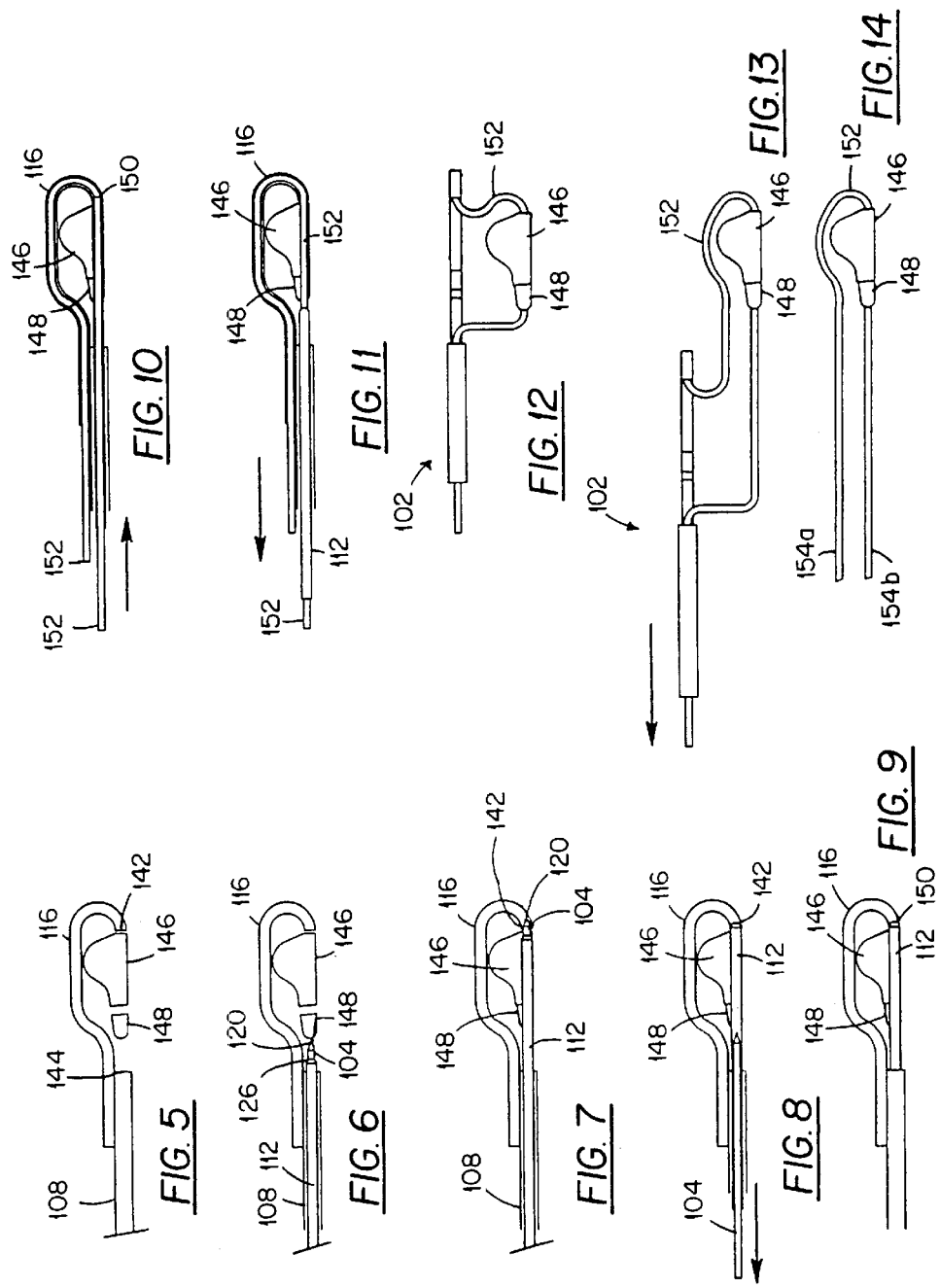

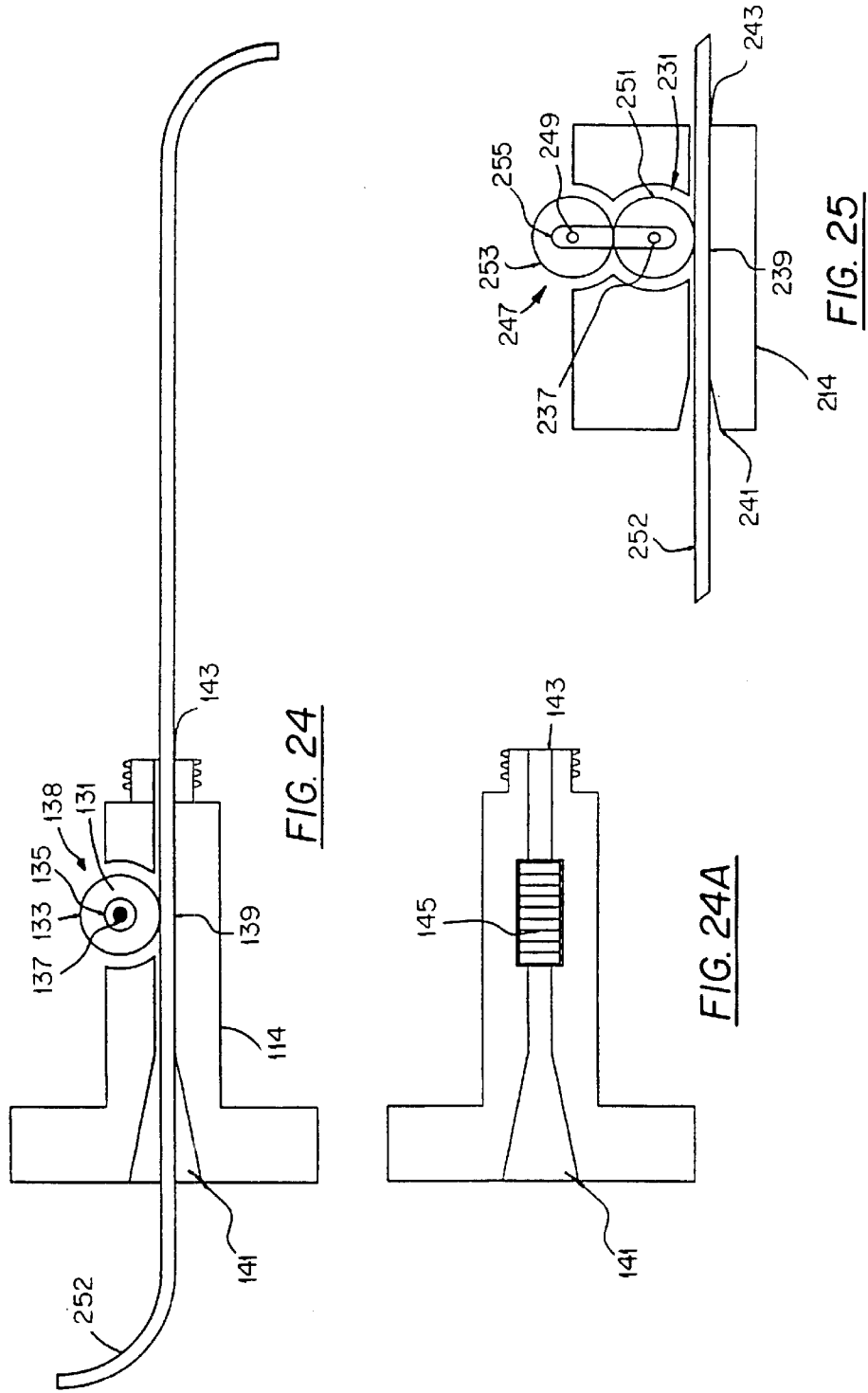

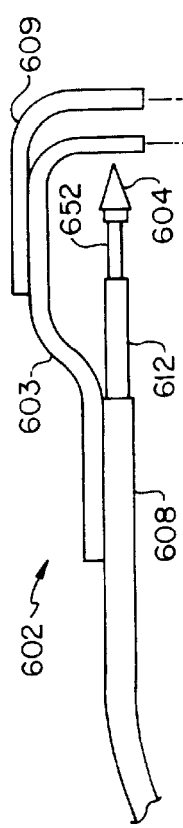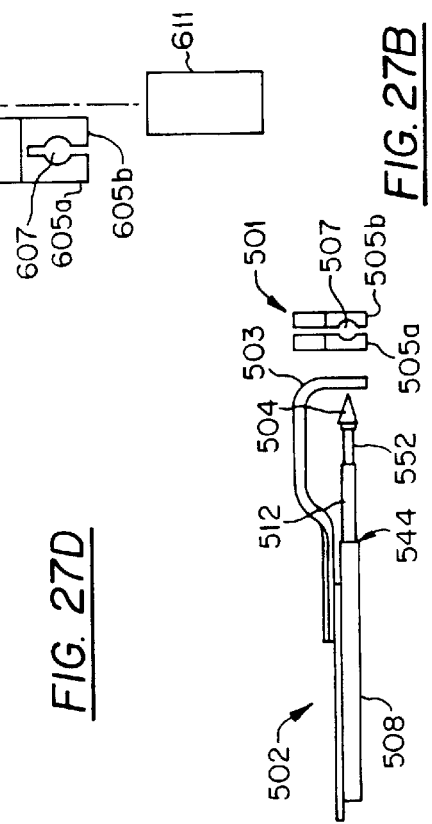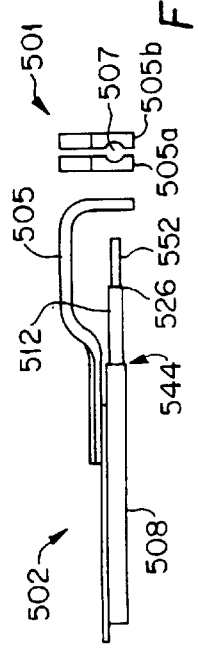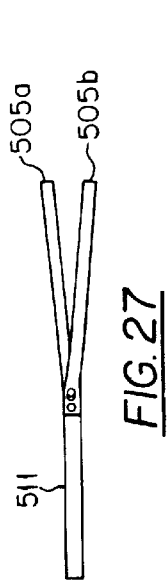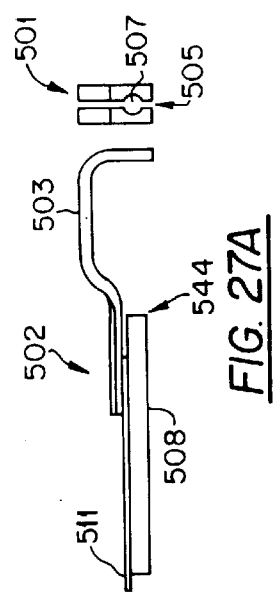

APPARATUS AND METHOD FOR REPAIRING OR REATTACHING SOFT TISSUE

FIELD OF THE INVENTION

The present invention relates generally to surgical devices and procedures and, more particularly, to an apparatus and method for suturing or repairing soft tissue injuries such as, for example, tears in the meniscus of the knee.

BACKGROUND OF THE INVENTION

The meniscus is the intra-articular cartilage found in the joint that separates the femur from the tibia, that is, the knee joint. Proper functioning of the knee joint depends, in part, upon the meniscus' ability to provide the joint with biomechanical stability and shock absorption during ambulation. Frequently, the meniscus is injured or torn, causing joint instability, pain in the knee, and resultant difficulties in ambulation. Two common surgical techniques are used in an effort to alleviate the pain associated with this type of injury. The first of these techniques is referred to as a menisectomy, which is the removal of the piece of tissue that has torn away from the greater meniscus. Depending upon the severity of the tear in the meniscal tissue, the surgeon may regard this as the best surgical option for the patient. The second technique involves the installation of a surgical implant into the segments of torn meniscal tissue to promote the fusion of the tissue and facilitate normal healing of the injury. In many cases, the surgeon will regard this latter option as more desirable than the former, since it is far less radical and potentially has fewer degenerative consequences, such as the development of osteoarthritis, for the patient over time.

Presently known devices and methods for delivering a surgical suture or suture-like implant into the meniscus or other soft tissue for repairing a tear in that tissue are unsatisfactory in several regards. Specifically, the prior art devices and methods may frequently prolong otherwise elegant surgical procedures by imparting the procedure with unnecessary mechanical inefficiencies. For example, the inability of prior art devices to pass suture or implant material into and out of soft tissue through the same body portal necessitates that a plurality of incisions be made into a patient's body, thereby increasing the level of trauma experienced by the patient during the procedure. Additionally, prior art rotating suture or implant feeding mechanisms employ counter-intuitive methods of operation that require the surgeon to rotate the wheel mechanism in a direction that is opposite the direction in which the surgeon desires to feed the suture or implant material. Moreover, currently known devices are incapable of accommodating variably dimensioned suture or implant materials, thereby presenting the surgeon with two equally undesirable options: First, the surgeon must use a single suture or implant material having a particular diameter or thickness, regardless of the needs of the patient; or, second, the surgeon must employ a plurality of surgical instruments, each capable of accommodating particularly dimensioned suture or implant material, which necessarily increases the number of steps required to complete the procedure and likely prolongs its duration.

In view of the foregoing, a need exists for an improved apparatus and method for repairing an injury to soft tissue which overcomes the shortcomings of the prior art. Thus, there is a need for an apparatus and method which enable a surgeon to pass a suture or other generally elongated implant material into and out of injured, torn, or detached soft tissue in essentially the same direction. There is also a need, especially in the case of arthroscopic surgeries, for an apparatus and method which are capable of passing a suture or implant material into and out of a joint space through a single body portal, thereby reducing the number of incisions required to accomplish the procedure. There is also a need for a single apparatus which is capable of delivering sutures or implant materials of various diameters or thicknesses. There is also a need for an apparatus having a rotating suture or implant feeding mechanism that permits the surgeon to rotate the feed mechanism in the same direction that the surgeon desires the suture or implant material to be fed. There is also a need for an apparatus capable of passing a plurality of tissue-piercing devices and suture legs through soft tissue at one time. There is also a need for an apparatus which can selectively orient the suture or implant material in either a horizontal, vertical, or diagonal direction, depending upon the needs of the patient and/or the desires of the surgeon. There is also a need for an apparatus and method for passing a suture or implant through soft tissue and grasping the end of the suture or implant on the opposite side of the soft tissue. Additionally, there is a need for an apparatus and method for passing a needle through a body portal and to the site of soft tissue injury while also protecting the surrounding tissue and nerves from damage that can be caused by the passage of that needle.

SUMMARY OF THE INVENTION

The present invention is an apparatus and method for delivering or installing a surgical suture or suture-like implant into soft tissue, such as the meniscus of the knee for example, for the reattachment or repair of that tissue. The apparatus and method of the invention facilitate ease of placement of the suture or implant by the surgeon, protect the surrounding tissue and nerves from damage during its use, and permit all suturing to occur through a single body portal. The present invention can be used in either open or arthroscopic surgical procedures and can be used for any tears in the meniscus or for other injuries to soft tissue which require a suture or implant to be passed through the tissue to facilitate reapproximation and healing of that tissue. In accordance with the invention, an injury to soft tissue, such as a tear in the meniscus of the knee joint or detachment of soft tissue from bone, is repaired through a single body portal by installing a surgical suture across the injury, tear, or detachment and passing that suture back through the body portal so that the suture can be joined and the injury, tear, or detachment can be reapproximated by the surgeon while working through the single body portal. It should be understood that the device of the instant invention can be used to pass suture or suture-like implants equally effectively. Thus, wherever the terms "implant" or "implant material" are used herein, it should be understood that the principles of the present invention apply equally to the use of all manner of surgical suture or suture-like materials.

The apparatus of the instant invention includes a guide structure which can be inserted through a body portal and brought into proximity with particular soft tissue. The guide structure is suitably configured to guide a length of suture or surgical implant material through the soft tissue and to bring legs of the length of implant material into proximity with each other. The guide structure includes a suitable, selectively moveable, tissue-piercing device, such as a needle for example, capable of piercing soft tissue and of being withdrawn from the soft tissue so that suitable suture or implant material then can be fed through the guide structure and into the soft tissue. The guide structure further is configured to be withdrawn toward the body portal and from the body in a manner which causes the guide structure to become disengaged from the length of implant material while leaving the length of implant material extending through the soft tissue and the legs of the length of implant material in proximity with each other. This then permits the surgeon, at his or her discretion, to join the approximated portions of implant material to accomplish the repair or reattachment of the soft tissue. However, it should be understood that the present invention does not require that the portions of the length of implant material be joined, nor is the present invention limited or restricted in any way to the joining of these portions of implant material.

In an exemplary embodiment of the instant invention, the guide structure further includes a pair of guide portions supported in spaced apart relation to each other and defining a gap which enables soft tissue to be disposed between the guide portions; a tissue-piercing device moveable in the gap between the guide portions and configured to pierce soft tissue disposed in the gap between the guide portions; and an introducer moveable in opposite directions in the gap between the guide portions. The introducer is moveable in one direction to form a passageway in the gap for guiding a length of implant material through soft tissue disposed within the gap and also is moveable in an opposite direction for re-establishing the gap between the guide portions. Thus, the gap that has been re-established between the guide portions enables the legs of the length of implant material to pass through the gap as the guide structure is withdrawn toward the body portal. The guide portions are suitably configured to guide the legs of the length of implant material into proximity with each other as the guide structure is withdrawn from the surgical site and toward the body portal.

In another exemplary embodiment of the present invention, the apparatus further includes a selectively engageable force applying device for feeding the suture or implant material from the proximal end of the guide structure to the distal end of the guide structure. The force applying device feeds suture or implant material through the guide structure by selectively engaging a length of implant material and thereby driving the length of implant material through the guide structure. The force applying device can also selectively disengage from the length of implant material to enable the length of implant material to slide more freely within the guide structure, as when the guide structure becomes disengaged from the length of implant material and is withdrawn from the body portal for example.

Other objects, features, and advantages of the present invention will become apparent to those skilled in the art from the following detailed description. It should be understood, however, that the detailed description and specific examples, while indicating exemplary embodiments of the present invention, are given for purposes of illustration only and not of limitation. Many changes and modifications within the scope of the instant invention may be made without departing from the spirit thereof, and the invention includes all such modifications.

BRIEF DESCRIPTION OF THE DRAWINGS AND EXHIBITS

The features and advantages of the instant invention reside in the details of construction and operation as more fully depicted, described, and claimed hereinafter; reference being had to the accompanying drawings and exhibits forming a part hereof, wherein like numerals refer to like parts throughout and wherein:

Exhibit 1 is a computer generated model of the human knee shown from the anterior aspect;

Exhibit 2 is a computer generated model of the superior aspect of the meniscus and the tibial plateau;

FIGS. 5–14 illustrate a method of using the embodiment of FIG. 1 to repair a torn meniscus;

FIG. 24 is a detailed cross sectional view of the feeding mechanism located on the introducer tube handle of FIG. 3;

FIG. 24A is a top view of the feeding mechanism of FIG. 24;

FIG. 25 illustrates another exemplary embodiment of the implant feeding mechanism located on the introducer tube handle;

Figure 1:
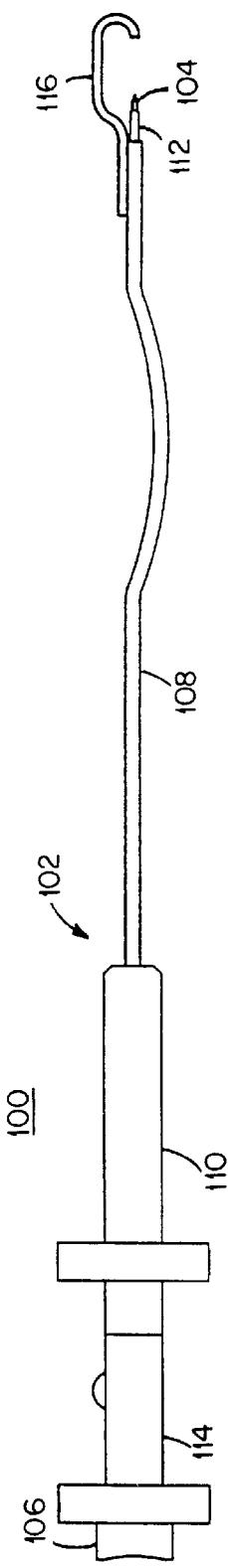
FIG. 1 is a side view of an exemplary embodiment illustrating the major components of the device.
Figure 28:
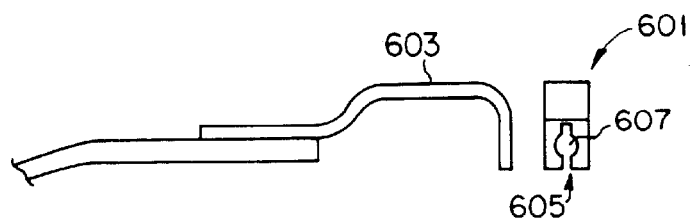
Figure 28A:
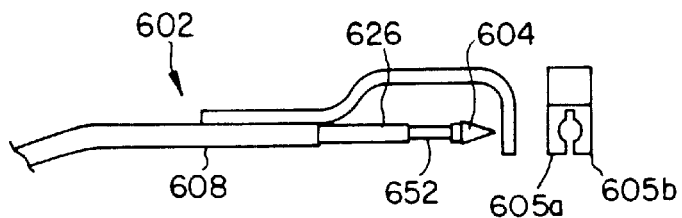
Figure 28B:
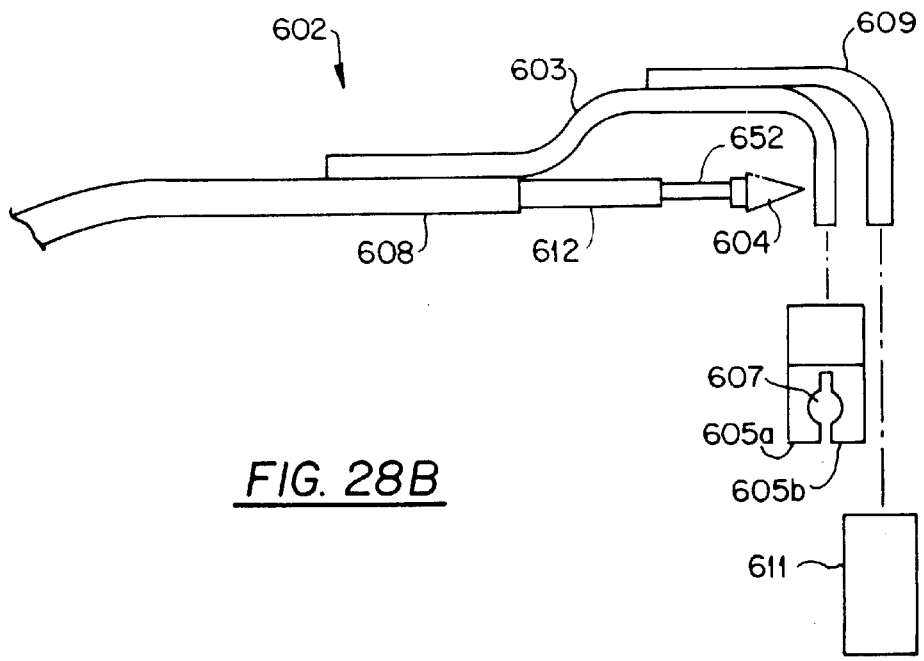
Figure 31:
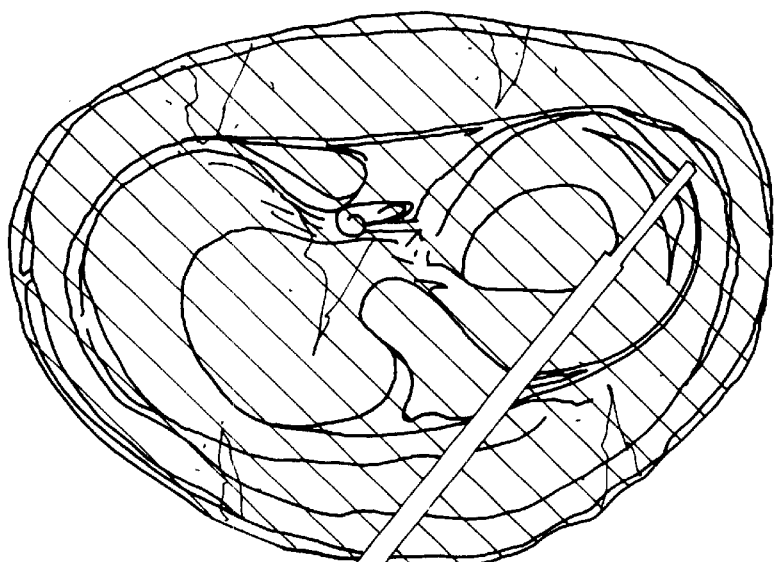
Figure 29:
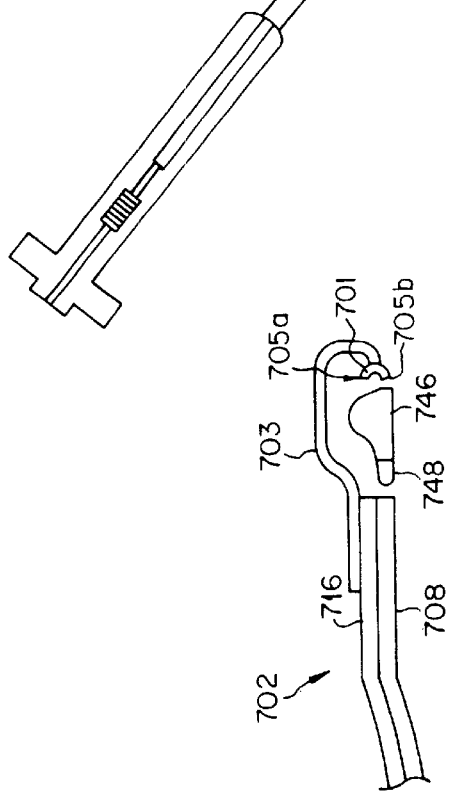
Figure 30:
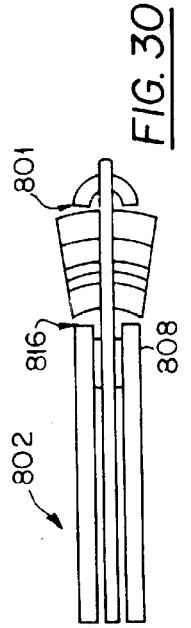
Figure 30A:
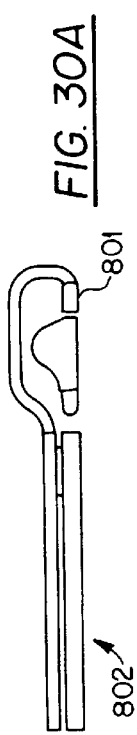
Figure 32:
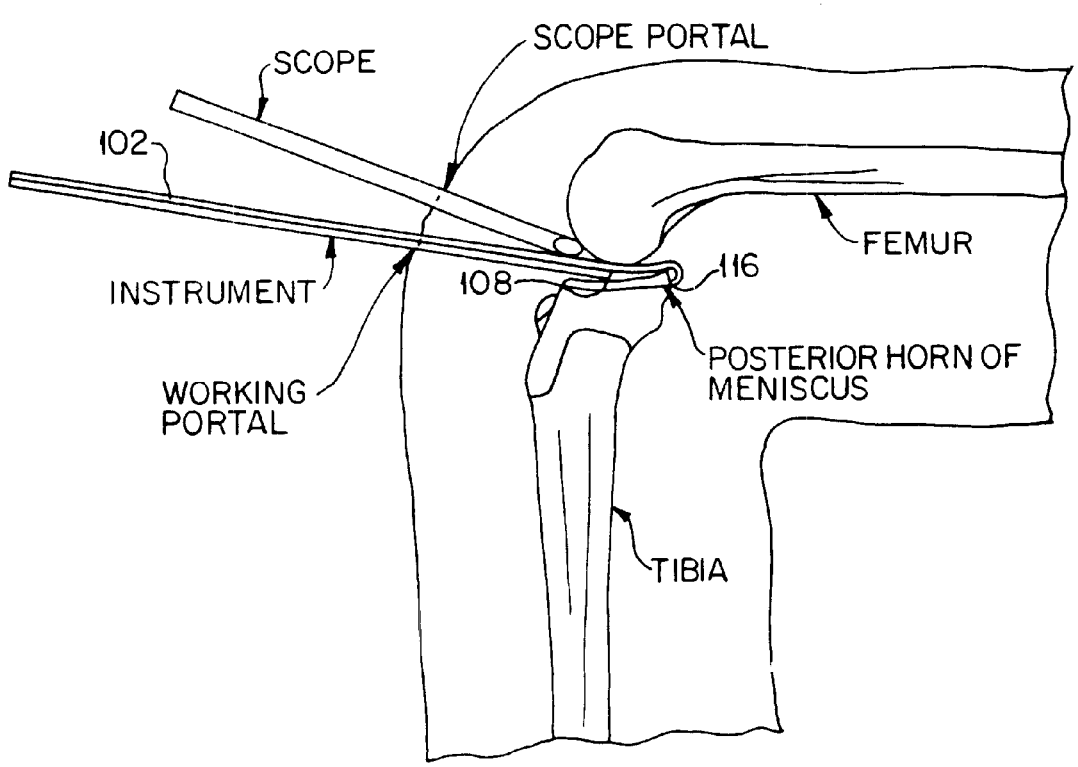

FIGS. 27, 27A, 27B, 27C, and 27D illustrate another exemplary embodiment of the device, wherein a receiver has a plurality of moveable elements for receiving and retaining a length of implant material guided through segments of torn soft tissue;

FIGS. 28, 28A, and 28B illustrate another exemplary embodiment, wherein a tissue-piercing device connected to a length of implant material is retained by a receiver formed by a plurality of flexible biased members;

FIG. 29 illustrates yet another embodiment of the device, wherein a plurality of tissue-piercing devices can pierce segments of torn tissue and allow a length of implant material to pass from a guide tube set, through segments of torn tissue, through a channel device, back through the tissue, and then into another guide tube set, in a manner which delivers a vertical stitch through the segments of torn tissue;

FIGS. 30 and 30A illustrate yet another embodiment of the device which allows a plurality of tissue-piercing devices to pass through segments of torn tissue and permits a length of implant material to pass through the torn tissue twice, in a manner which delivers a horizontal stitch through the segments of torn tissue;

FIG. 31 illustrates an exemplary embodiment of the device superimposed on a top cross-sectional view of a meniscal tear; and FIG. 32 is a diagram depicting a lateral view of the knee and illustrating the use of the exemplary embodiment of the device shown in FIG. 1 to repair the meniscus.

DETAILED DESCRIPTION

The present invention is an apparatus and method for delivering or installing a surgical suture or suture-like implant material into soft tissue, such as the meniscus of the knee for example, for the reapproximation or reattachment of that tissue. The device is particularly useful for repairing torn or detached intra-articular tissue, such as the meniscal cartilage of the knee joint, and can be used in either open or arthroscopic surgical procedures. It should be understood that the instant invention is not limited to the use of surgical suture. The present invention includes the use of other implants or implant materials, as now known in the art or may be designed in the future, which may have similar physical or chemical properties to surgical suture but are better able to promote fixation and healing of soft tissue. Wherever the terms "implant" or "implant materials" are used herein, it should be understood that these terms mean all manner of surgical suture or suture-like materials, including, without limitation or restriction, non-bioabsorbable or bioabsorbable materials, further including allograft, autograft, or xenograft materials.

FIGS. 1 through 4 illustrate the major components of an exemplary embodiment of the device of the instant invention. FIG. 1 is a side view of the device 100 which generally illustrates the manner in which the various components are related to each other when the device 100 is in use. The device 100 comprises a guide structure 102, which further comprises a tissue-piercing device 104, a tissue-piercing device handle 106, a pair of guide portions 108 and 116, a guide structure handle 110, an introducer 112, and an introducer handle 114.

Figure 2:
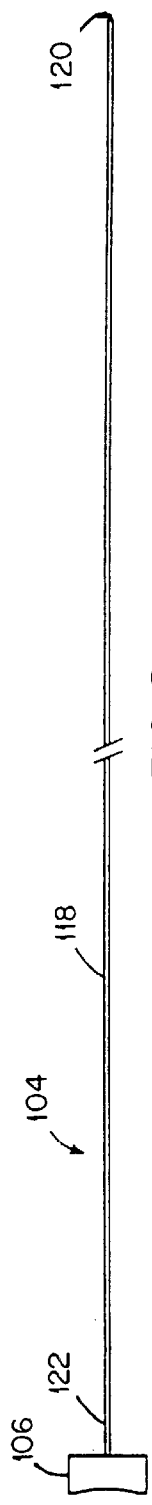
FIG. 2 illustrates the tissue-piercing device of the embodiment of FIG. 1.

FIG. 2 better illustrates the tissue-piercing device 104 of FIG. 1. The tissue-piercing device 104 can be any suitable structure for piercing the soft tissue (not shown) through which a surgeon intends to pass suture or implant material (not shown). The tissue-piercing device 104 can be, for example, a needle or other suitable fine gauged structure. Preferably, the tissue piercing device 104 is formed at the distal end of an elongated cylindrical rod or shaft 118 which preferably can slide in opposite directions within the introducer 112. The shaft 118 preferably is configured to enable the tissue piercing device 104 to move in one direction within a gap between the guide portions 108 and 116 to pierce soft tissue and to move in an opposite direction for withdrawing the tissue piercing device 104 from the introducer 112, so that a length of implant material can be inserted into and moved within and through the introducer 112. Shaft 118 preferably has an outer diameter that is similar to that of the suture or suture-like material which the surgeon intends to pass through the injured or torn tissue. The suture or suture-like material may be of any suitable thickness or diameter but preferably has a diameter ranging from about 0.008 inches to about 0.030 inches. The distal tip 120 of the tissue-piercing device 104 preferably has a relatively sharp point and a generally conical shape that preferably is similar to that of a sewing needle or a pin to facilitate the piercing of the injured soft tissue by the tissue-piercing device 104. The tissue-piercing device 104 preferably has a handle 106 permanently affixed to its proximal end 122, thereby enabling the surgeon to control the tissue-piercing device 104 with minimal damage to the surgeon's surgical glove (not shown). The needle or tissue-piercing device 104 preferably is moveable in opposite directions within the introducer 112 and the guide portions 108 and 116, such that the needle or tissue-piercing device 104 is moveable in one direction for piercing the segments of torn tissue and in another direction for withdrawing the needle or tissue-piercing device 104 from the segments of torn tissue to enable a length of implant material to be guided through the segments of torn tissue.

Figure 3:
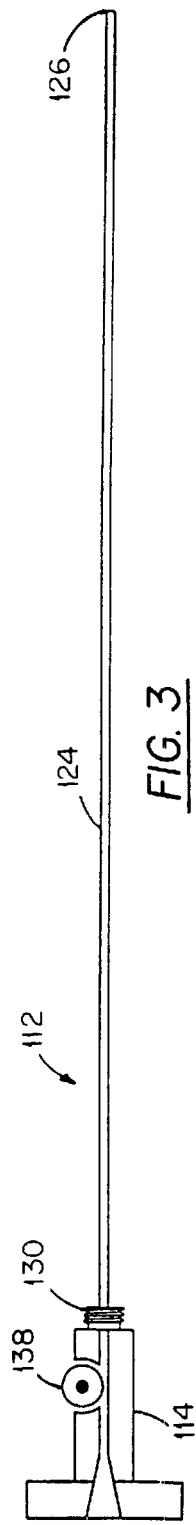
FIG. 3 illustrates the introducer tube of the device of FIG. 1, including an implant feeding mechanism and an introducer tube handle having a threaded member for attaching the introducer tube handle to the guide structure handle of FIG. 4.

FIG. 3 better illustrates the introducer 112 of FIG. 1. In one embodiment, the introducer 112 is preferably an elongated cylindrical tube 124 having an internal diameter that is preferably similar to that of the outer diameter of the tissue-piercing device 104 of FIG. 2. The introducer tube 112 may have any suitably configured distal end portion, but preferably has a conical or chamfered distal end portion 126 capable of following the tissue-piercing device 104 through soft tissue. In this manner, the introducer tube 112 can pass through injured soft tissue when the introducer tube 112 is placed concentrically over the tissue-piercing device 104 of FIG. 2. This configuration further permits the introducer tube 112 to extend at least partially into the guide portion 116 of FIG. 4 to form, at least temporarily, a passageway extending substantially between the introducer tube 112 and the guide portion 116 for guiding a length of implant material through the torn tissue. The introducer tube 112 also preferably has an introducer tube handle 114 rigidly attached to its proximal end 128, which handle 114 preferably has a suitable fastener means, such as threaded member 130, for attaching the introducer tube handle 114 to a suitable corresponding fastener means, such as a corresponding female threaded portion 132, shown on guide structure handle 110 in FIG. 4, for attaching the proximal end 134 of the guide structure handle 110 to the introducer tube handle 114. The introducer tube 112 preferably is configured to receive and guide a length of implant material, and the introducer tube handle 114 preferably comprises a force applying device, such as feeding mechanism 138. Feeding mechanism 138 is preferably configured to apply a suitable amount of directional force to a length of implant material disposed within the introducer tube 112 to move the length of implant material within and through the introducer tube 112. Thus, feeding mechanism 138 provides a surgeon with means for advancing a suture or suture-like material from the proximal end of the device 100, shown in FIG. 1, to the distal end of the device 100 when the tissue-piercing device 104 preferably has been withdrawn from the device 100 after the segments of torn tissue have been suitably pierced. In addition, the feeding mechanism 138 provides the surgeon with suitable means for retracting or reversing the direction of the suture or implant material from the distal end to the proximal end of the guide structure 102 of FIG. 1. The feeding mechanism 138 is described in greater detail below with reference being had to FIGS. 24, 24A, and 25.

Figure 4:
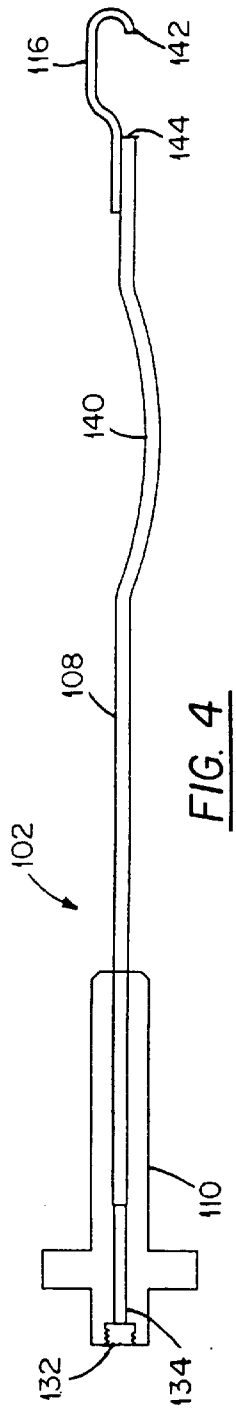
FIG. 4 illustrates the assembly of the guide structure, including the guide tubes and the guide tube handle, wherein the guide tube handle has a female threaded portion adapted to attach the introducer tube handle of FIG. 3.

FIG. 4 better illustrates the assembly of the guide structure 102 of FIG. 1. Preferably, guide structure 102 is configured to be at least partially located within an articular space, such as a knee joint, to facilitate installation of an implant in soft tissue, such as the meniscus, located within that articular space. Preferably, the guide structure 102 comprises a pair of guide portions 108 and 116, which are preferably a pair of guide tubes 108 and 116. Each guide tube 108 and 116 preferably is disposed in a common plane which has a thickness equal to the largest outer diameter of the pair of guide tubes 108 and 116. Preferably, a gap is formed between the guide tubes 108 and 116, which gap also is located within this common plane. The introducer tube 112 of FIG. 3 and the tissue-piercing device 104 of FIG. 2 also are moveable within this common plane and preferably are configured to enable a length of implant material to be moved within the common plane. Preferably, the thickness of the common plane is dimensioned to enable the pair of guide tubes 108 and 116 to be at least partially located within an articular space, such as a knee joint (not shown).

As further illustrated in FIG. 4, each of the guide tubes 108 and 116 preferably comprises an elongated cylindrical tube having an internal diameter similar to that of the outer diameter of the introducer tube 112 of FIG. 3. In one embodiment, the guide tube 108 preferably has at least one bend 140 which enables the device 100 of FIG. 1 to be manipulated or maneuvered around anatomical structures, such as bones, and other anatomical features that may hinder or prevent straight or axial passage of the device 100 through the body of a patient. In this embodiment, the introducer tube 112, shown in FIG. 3, preferably is of suitable flexibility to permit the introducer tube 112 to move lengthwise through the at least one bend in the guide tube 108 and/or through any bends in the guide tube 116, as required. In one embodiment, guide tube 116 preferably is attached or fixed to the guide tube 108. The guide tube 116 is preferably an elongated cylindrical tube which preferably is bent in such a manner that its distal end 142 is generally facing the distal end 144 of the guide tube 108. Preferably, the guide tube 116 also has one or more bends which permit facilitated manipulation or extension of the device around anatomical structures or masses of the body. The guide tube 116 preferably is attached rigidly to the outer diameter of the guide tube 108 so that the proximal end of the guide tube 116 generally faces the same direction as the proximal end of the guide tube 108. Preferably, the distal ends 142 and 144 of the guide tube 116 and the guide tube 108, respectively, have openings which are spaced apart and aligned with each other to allow free movement or passage of the tissue-piercing device 104 of FIG. 2, the introducer tube 112 of FIG. 3, and suture or suture-like material through the guide tube 108 and the guide tube 116. The proximal end 134 of the guide structure 102 preferably is attached rigidly to a guide structure handle 110. As noted above with respect to FIG. 3, the guide structure handle 110 preferably includes a fastener means, such as a female threaded portion 132, located on the proximal end 134 of the guide structure handle 110 for matingly and engagingly attaching a suitable corresponding fastener means, such as threaded member 130, on the introducer tube handle 114, shown in FIG. 3.

FIGS. 5 through 14 describe the general method of using the device 100 of FIG. 1. Generally, a method for installing an implant in soft tissue comprises the steps of providing a guide structure, locating the guide structure in a selected orientation with respect to the soft tissue, operating the guide structure to guide a length of implant material through the soft tissue, and withdrawing the guide structure from the soft tissue in a manner which maintains the implant material in the soft tissue and disengages the guide structure from the length of implant material with the legs of the length of implant material in proximity to each other. In a preferred embodiment, the method for installing an implant in soft tissue further comprises the step of manipulating the guide structure into a selected orientation after the length of implant material has been guided through the soft tissue. Preferably, the selected orientation enables the friction between the length of implant material and the soft tissue to cause the guide structure to disengage from the length of implant material as the guide structure is withdrawn from the soft tissue.

FIG. 5 illustrates the first step of a preferred method for installing an implant in soft tissue in accordance with the principles of the present invention. It should be understood that while the method of the present invention is exemplified with reference to the repair of a meniscal tear, the principles of the instant invention are applicable to the repair and/or reattachment of a variety of soft tissues and are not intended to be limited to the repair of meniscal tissue. FIG. 5 shows a cross sectional view of the posterior horn of the meniscus 146 placed between the distal end 144 of the guide tube 108 and the distal end 142 of the guide tube 116. In the illustrated example, the proximal end of the device 100 preferably is inserted concentrically through a portal (not shown) located in a generally anterior aspect of the knee (not shown). The distal end 142 of guide tube 116 is placed on the posterior aspect of the meniscus and is aligned with the tear that is to be repaired, as better seen in FIG. 31. Preferably, the distal end 144 of guide tube 108 is directed toward the torn segment of the meniscus 148 so that the implant material (not shown) preferably passes directly through the two segments 148 and 146, respectively, of the meniscus.

Referring next to FIG. 6, after the device is placed in the desired location over the meniscus, the tissue-piercing device 104 and the introducer tube 112 preferably are slid concentrically through the guide tube 108 until the distal tip 120 of the tissue-piercing device 104 contacts the torn meniscal tissue 148. The distal end 126 of the introducer tube 112 preferably trails or follows immediately behind the conical distal tip 120 of the tissue-piercing device 104 as the tissue-piercing device 104 passes through the soft tissue, thereby reducing potential entrapment of the introducer tube 112 within the meniscal tissue.

Turning next to FIG. 7, the tissue-piercing device 104 and introducer tube 112 preferably are then forced through the torn segment of meniscal tissue 148 and the intact meniscal horn tissue 146 until the distal tip 120 of the tissue-piercing device 104 preferably passes the distal end 142 of the guide tube 116 and advances no further. As illustrated in FIG. 8, the introducer tube 112 preferably is advanced until contact is made with the distal end 142 of the guide tube 116. The tissue-piercing device 104 preferably is then retracted from the device 100 in the direction indicated by the arrow shown in FIG. 7.

Preferably, as illustrated in FIGS. 9 and 10, once the introducer tube 112 and the guide tube 116 are proximate each other at junction or passageway 150, and the tissue-piercing device 104 has been retracted as shown in FIG. 8, a clear path is established through the passageway 150, which permits a suitable length of suture, suture-like material, or similar implant material 152 to be fed or passed through the passageway 150 and into the guide tube 116 to deliver an implant or stitch through the torn segments of meniscal tissue 148 and 146. Preferably, this suture or implant 152 is delivered by the feeding mechanism 138, as shown in FIG. 1 and described in greater detail below with reference being had to FIGS. 22A, 22B, and 23.

Once the desired length of suture or implant has been passed through the soft tissue, the introducer tube 112 preferably is retracted toward the body portal in the direction illustrated by the arrow shown in FIG. 11. Preferably, as illustrated in FIG. 12, the guide structure 102 then is manipulated into a selected orientation, such as being turned 90 degrees for example, within the joint space. As better seen in FIG. 13, this selective manipulation and orientation of the guide structure 102 preferably allow the guide structure 102 to utilize the friction created between the length of implant material 152 and the segments of torn tissue 148 and 146 to disengage the length of implant material 152 from the guide structure 102 as the guide structure 102 is retracted toward the single body portal (not shown) in the direction indicated by the arrow shown in FIG. 13. As illustrated in FIG. 14, this method of retracting the guide structure 102 ensures that the implant material 152 remains stitched through the two segments of meniscal tissue 148 and 146, permitting the two legs or end portions 154a–b of the suture or implant material 152 to be connected in a manner that facilitates the fusion and healing of the segments of meniscal tissue 148 and 146. It should be noted that the particular method of connecting the legs or end portions 154a–b of implant material 152 is beyond the scope of the present invention.

Figure 15:
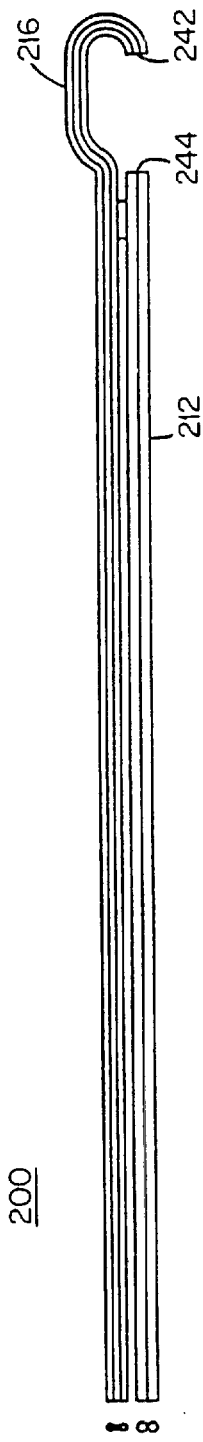
FIG. 15 illustrates the guide tubes of another exemplary embodiment of the device having a plurality of introducer tubes and guide tubes which enable a plurality of tissue-piercing devices to pass through torn tissue simultaneously.
Figure 16:
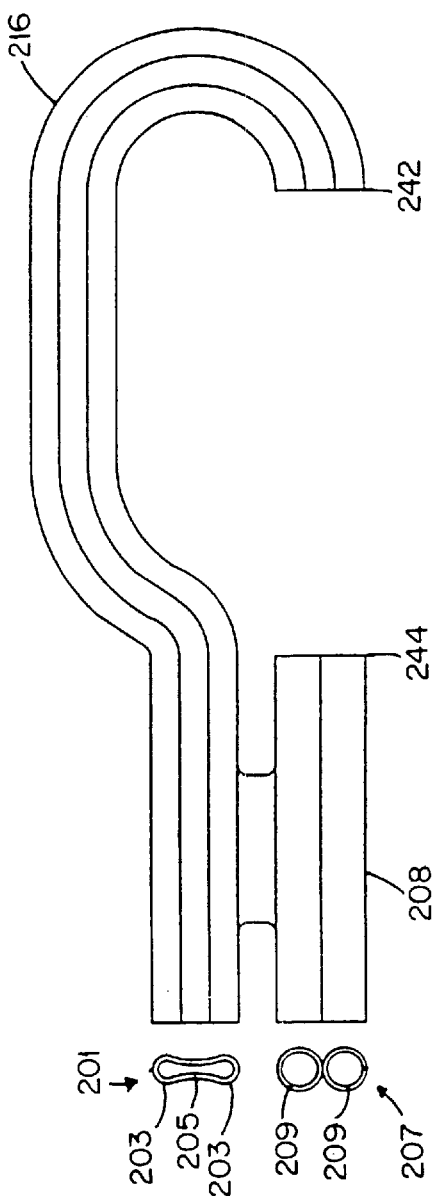
FIG. 16 is a detailed view of the device of FIG. 15 illustrating the distal end of the device and cross sectional views of the guide tubes.

FIGS. 15 and 16 illustrate an exemplary embodiment of the device 200 of the instant invention. The device 200 preferably includes a pair of guide portions comprising a pair of guide tube sets 208 and 216, each of which further comprises a pair of adjacent guide tubes 209 and 203, respectively. Preferably, the guide tube sets 208 and 216 are configured to enable portions of a length of implant material to be guided through soft tissue. Preferably, at least one of the pair of guide portions, such as guide tube set 216, is further configured to maintain the legs of the portions of implant material in adjacent spaced relation to each other as the portions of implant material are guided through the soft tissue. The configuration of the guide tube sets 208 and 218 preferably permit a plurality of tissue-piercing devices and a plurality sutures or implants, or suture or implant legs, to pass through the torn tissue simultaneously.

FIG. 16 is a detailed view of the distal end of the device 200 shown in FIG. 15. This embodiment preferably is used in a different manner than the embodiment illustrated in FIG. 1 in that the suture or implant material is fed from the guide tube set 216 to the guide tube set 208, rather than from the guide tube 108 to the guide tube 116 as described above with reference to FIGS. 9 and 10. In this embodiment, as seen in cross sectional view 201, at least one of the pair of guide portions, such as the guide tube set 216, preferably comprises a single lumen tube structure defining a pair of adjacent guide tube portions 203 having a reduced central portion 205 joining the pair of adjacent guide tube portions 203. Each of the pair of adjacent guide tube portions 203 is configured to guide a leg or portion of a length of implant material (not shown) in a lengthwise direction, and the central portion 205 is configured to maintain the pair of adjacent guide tube portions 203 in spaced relation to each other, thereby allowing a connecting portion of the length of implant material to slide sideways through the central portion 205 with an interference fit. Thus, preferably a plurality of legs or portions of a length of suture or implant material can be simultaneously fed into the guide tube set 216 and through torn tissue in a spaced apart manner. The cross sectional view 207 of the guide tube set 208 illustrates a preferred double lumen structure having adjacent guide tubes 209 through which legs or portions of implant material can pass subsequent to passing through the guide tubes 216 and the torn soft tissue.

Figure 17:
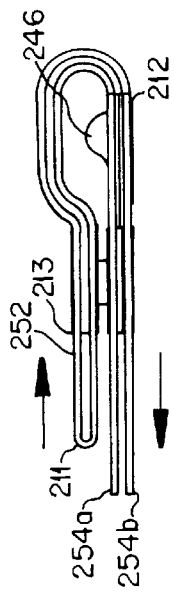
FIGS. 17–23 illustrate a method of using the device of FIGS. 15 and 16, wherein a plurality of tissue-piercing devices can be passed through torn tissue simultaneously.

FIGS. 17 through 23 illustrate an exemplary method of using the device 200 shown in FIG. 15. The method of using this embodiment is a modified version of the method described above with reference to FIGS. 5 through 14. As illustrated in FIG. 17, the device preferably is placed over the meniscus with the distal end 242 of the guide tube set 216 contacting the posterior aspect of the meniscus 246 and the distal ends 244 of the guide tube set 208 generally directed toward the torn piece of meniscal tissue 248. As better seen in FIG. 18, the tissue-piercing devices 204 preferably perform a similar function and are used in an identical manner to that described above with reference to FIGS. 5 through 14.

Figure 18:
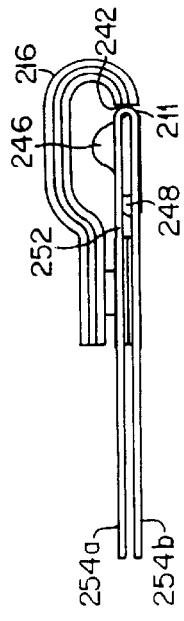
Figure 19:
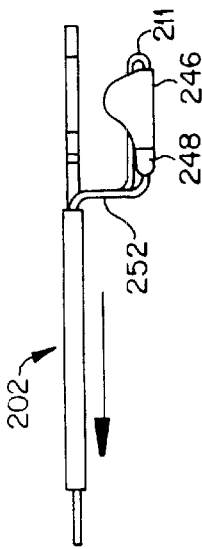

FIG. 19 illustrates a plurality of introducer tubes 212 concentrically inserted within the guide tube set 208 and fully extended toward the distal end 242 of guide tube set 216. The method of passing the introducer tubes 212 through the segments of torn tissue is as described above with reference to FIGS. 6 through 8, notwithstanding the difference of using a plurality of introducer tubes 212 and a plurality of tissue-piercing devices 204, as shown in FIG. 18. In a manner similar to that described above with reference to FIGS. 8 through 10, the method of using the embodiment of FIG. 15 preferably places the introducer tubes 212 and the guide tube set 216 proximate each other at a junction or passageway 250. Thus, after the tissue-piercing devices preferably have been retracted in a manner similar to that described above with reference to FIG. 8, a clear path is established through the passageway 250, which permits a plurality of legs or portions of a suitable length of suture, suture-like material, or similar implant material to be fed or passed through the guide tube set 216, through the passageway 250, and then into the introducer tubes 212, effectively delivering a suture or stitch through torn segments of meniscal tissue.

Figure 20:
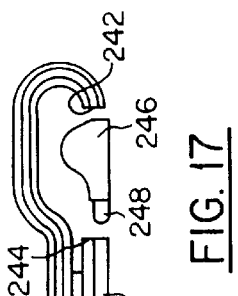
Figure 21:
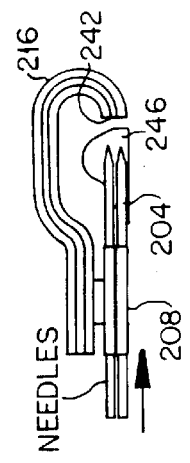
Figure 22:
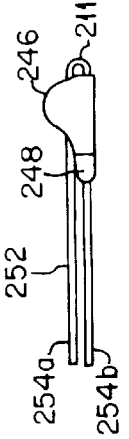
Figure 23:
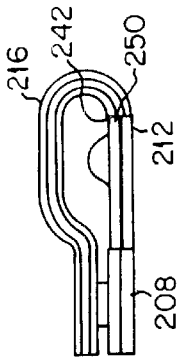

FIG. 20 illustrates a suture or implant 252, having a connecting portion 211 and legs or end portions 254a–b, being advanced, as indicated by the arrows, through the guide tube set 216, through the segments of meniscal tissue 246 and 248, and into the introducer tubes 212 within the guide tube set 208. Preferably, as the suture or implant 252 continues to be advanced by a surgeon pulling on the end portions 254a–b, the loop or connecting portion 211 eventually contacts the proximal ends 213 of the guide tube set 216 and has an interference fit within the guide tube set 216. As illustrated in FIG. 21, as the suture or implant 252 is advanced further, the loop 211 eventually clears the distal end 242 of the guide tube set 216 and contacts the posterior aspect of the meniscal horn tissue 248. Then, as seen in FIG. 22, the guide structure 202 preferably is selectively oriented, or turned, and retracted toward the body portal, as described above in greater detail with reference to FIGS. 12 through 14. In this manner, a complete stitch of the implant material 252 is delivered through the two segments of torn meniscal tissue with a loop 211 on the posterior aspect of the meniscus 248. As illustrated in FIG. 23, the plurality of legs or end portions 254a–b of implant material 252 are then positioned so that they easily may be connected to facilitate the fusion and healing of the segments of meniscal tissue 248 and 246.

FIGS. 24 and 24A are detailed views of an exemplary embodiment of the inventive suture or implant feeding mechanism 138, as shown in FIG. 1. The feeding mechanism is a force applying device, which preferably includes a drive wheel 131 extending at least partially into the handle 114 and the introducer tube 112. Preferably, the drive wheel 131 is rotatable about an axis or axle 137 and has an external surface suitably configured for applying force to and moving a length of implant material 252 through the introducer tube 112 of FIG. 1. The drive wheel 131 preferably has an outer diameter 133 and an inner diameter 135, wherein the inner diameter 135 is larger than the outer diameter of the axle 137. The suture guide 139 within the introducer tube handle 114 has a proximal suture introducing end 141 and a distal suture receiving end 143. In accordance with one embodiment of the invention, the axle 137 and the drive wheel 131 are both selectively moveable in one direction transverse to the length of implant material 252 within the introducer tube 112 to engage and move or drive the length of implant material and are moveable in an opposite direction to disengage from the length of implant material to allow the length of implant material to slide within the introducer tube 112. In another embodiment, the drive wheel 131 is selectively moveable relative to the axle 137 in one direction transverse tot eh length of implant material 252 within the introducer tube 112 to engage and move or drive the length of implant material and is moveable in an opposite direction to disengage from the length of implant material to allow the length of implant material to slide within the introducer tube 112. In both of these embodiments, a surgeon is thereby permitted to depress and rotate the drive wheel 131 to move the length of implant material 252 through the introducer tube 112 by frictionally engaging the implant material 252 with the drive wheel 131. In this manner, a surgeon also can selectively utilize implant materials 252 of varying thickness or diameters with a single device, rather than requiring a particular device for each of the desired suture or implant diameters, since the feeding mechanism 138 preferably permits selective depression of the drive wheel 131, as required by the diameter or thickness of the employed implant material 252. As illustrated in the top view of FIG. 24A, the outer surface 133 of the drive wheel 131 preferably has a suitably configured surface, such as teeth or serrations 145, for effectively gripping and moving the suture or implant material through the device.

FIG. 25 illustrates an alternative embodiment of the suture or implant feeding mechanism of the instant invention. In this configuration, the feeding mechanism or force applying device preferably includes a second drive wheel 247 rotatable about an axis 249 parallel to the axis 237 of a first drive wheel 231. The second drive wheel 247 preferably has an outer surface that engages the first drive wheel 231 in a manner that rotates the first drive wheel 231 in a direction opposite that of the second drive wheel 247. Thus, when a surgeon depresses and rotates second drive wheel 247, a rotational frictional force is applied through second drive wheel 247 to first drive wheel 231, which ultimately results in movement of the implant material 252 through the guide structure in the same direction that the surgeon rotates the second drive wheel 247. The addition of the second drive wheel 247 to the feeding mechanism 238 enables the suture or implant material 252 to advance, reversibly, in the same direction that the second drive wheel 247 is rotated. Preferably, each drive wheel 231 and 247 has a suitably configured surface, such as teeth or serrations, on its outer diameter to engage the drive wheels. In this manner, the drive wheels 231 and 247 preferably act as gears to grip and move the suture or implant material 252 through the guide structure. The drive wheels 231 and 247 have outer diameters 251 and 253, respectively, and axles 237 and 249, respectively, which preferably are rigidly attached to a pair of directly opposed slots 255 on the introducer handle 214. The slots 255 enable the drive wheels 231 and 247 to rotate and to move in a downward or transverse direction to conform selectively to varying suture diameters and thicknesses, as more fully described above with reference to FIGS. 24 and 24A.

Figure 26:
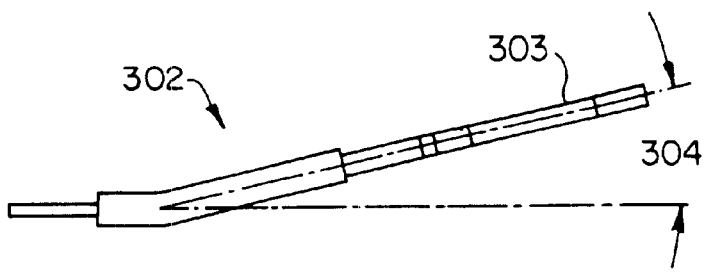
FIGS. 26 and 26A illustrate exemplary embodiments of the device having alternative orientations or bends in the guide structure which facilitate manipulation of the device around anatomical structures of the body.
Figure 26A:
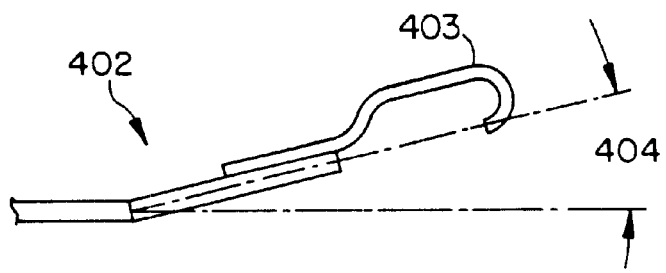
Figure 26B:
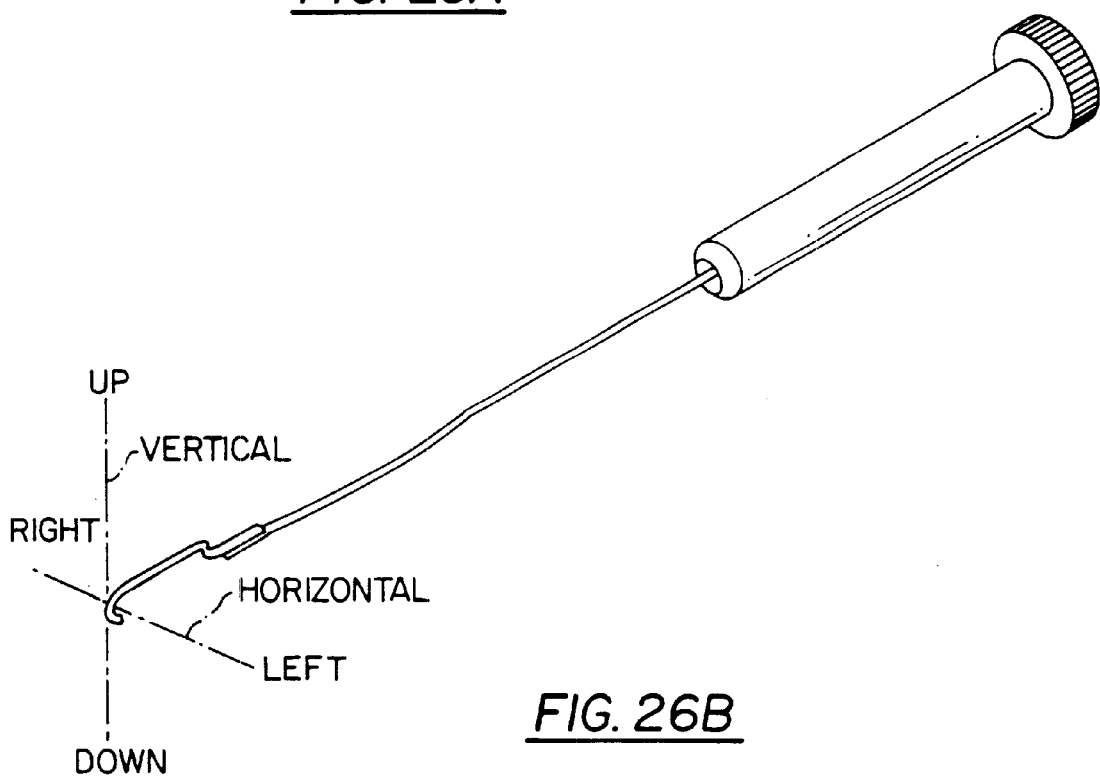
FIG. 26B is an isometric view of the device of FIG. 4 defining the directions referred to herein.

As noted above with reference to FIG. 4, a plurality of angular configurations or bends in the guide structure and/or the guide tube(s) of the instant invention may be required to allow the instrument to conform to particular anatomical features or structures of the human body. FIGS. 26 and 26A illustrate exemplary embodiments of the device of the instant invention which include these types of bends in the guide structure. Although various embodiments of the present invention as described herein position the distal end of the guide structure in a generally horizontal manner, this configuration is not necessarily desirable in all cases. Depending upon such factors as the particular anatomical structures surrounding the site of the surgical procedure or the location of the body portal through which the procedure is conducted, the guide structure may preferably be oriented in an upward, downward, leftward, or rightward direction, as these directional orientations are generally illustrated and defined in FIG. 26B. FIG. 26 illustrates an exemplary angular bend in the guide structure 302 that allows the distal end 303 of the device to be directed generally leftward with an angle 304 when the guide structure 302 is maintained in a generally horizontally position. FIG. 26A illustrates another exemplary angular bend in the guide structure 402 that allows the distal end 403 of the device to be directed generally upward with an angle 404 when the guide structure 402 is maintained in a generally horizontally position. It should be understood that a variety of angular configurations of the inventive guide structure are possible and all such configurations are intended to come within the spirit and scope of the present invention. The present invention is not intended to be limited to the exemplary angular configurations illustrated and described herein.

FIGS. 27 and 27A illustrate a top and a side view, respectively, of another exemplary embodiment of the present invention, wherein the guide structure 502 preferably includes a guide tube 508 configured to guide a length of implant material through segments of torn soft tissue and a receiver 501 connected to the guide tube. Preferably, the guide structure further comprises a support device 503 connected with the receiver 501, and, preferably, receiver 501 further comprises a receiving portion 505 configured to receive a length of implant material guided through segments of torn soft tissue. The receiving portion 505 preferably includes a plurality of elements 505a–b configured to form an opening for receiving and retaining a length of suture or implant material guided through segments of torn tissue. In the illustrated example, elements 505a–b are selectively moveable relative to each other to form an opening 507 and are controlled by a manipulator 511 on the support device 503. Preferably, the manipulator 511 is coupled to a hand-operated mechanism, such as a trigger, which is preferably located on the handle or proximal end (not shown) of the guide structure so that a surgeon may control the elements 505a–b at a distance from the surgical site.

As illustrated in FIGS. 27B and 27C, the plurality of elements 505a–b preferably are used to grasp a suture or suture-like material 552 or a needle or other tissue-piercing device 504 that is suitably affixed or swedged to an implant or suture 552. In this embodiment, if a needle or other tissue-piercing device 504 is suitably affixed or swedged to an implant 552, the tissue-piercing device 504 is suitably configured and/or dimensioned such that the entire length of tissue-piercing device 504 passes through the soft tissue and is grasped and retained by the receiver 501. As the elements 505a–b are selectively manipulated by the manipulator 511, the elements 505a–b preferably are positioned such that when the suture material or implant 552 or the tissue-piercing device 504 affixed to a suture or implant 152 passes through the distal end 544 of the guide tube 508, the implant 552 or tissue-piercing device 504 affixed to an implant 552 directly contacts the plurality of elements 505a–b, thereby preventing damage to soft tissue behind the plurality of elements 505a–b. When the plurality of elements 505a–b are separated by the manipulator 511, the opening 507 is sufficient for the implant 552 and/or the tissue-piercing device 504 affixed to an implant 552 to pass between the plurality of elements 505a–b and into the opening 507. The plurality of elements 505a–b are suitably shaped to grasp the implant 552 and/or the tissue-piercing device 504 affixed to an implant 552. Thus, as the plurality of elements 505a–b are opened or separated by the manipulator 511, the implant 552 or the tissue-piercing device 504 affixed to an implant 552 is advanced through the guide tube 508 to the plurality of elements 505a–b until sufficient implant material 552 has passed between the plurality of elements 505a–b to allow the plurality of elements 505a–b to grasp and retain the tissue-piercing device 504 or implant material 552. Finally, the guide structure 502 can be selectively oriented and retracted from the surgical site and/or the body portal, as described above with reference to FIGS. 12 through 14, leaving a suitable length of the implant material 552 within the segments of torn soft tissue.

In the embodiment illustrated in FIG. 27B, and as noted above, the needle 504 is permanently attached or swedged to the suture or implant material 552. A rigid member (not shown) advances the needle 504 through guide tube 508 and into the injured tissue. A modified introducer tube 512 can be placed concentrically over the implant material 552 to remotely transfer an axial force from the surgeon to push the needle 504 and the implant material 552 through the soft tissue and into the pair of elements 505a–b. Unlike the introducer tube 112 of FIG. 1, the introducer tube 512 preferably is modified such that the distal end 526 is blunt and does not have a chamfer.

In another embodiment, as illustrated in FIG. 27D, the guide structure 502 preferably comprises a support device 503 which further includes a support member 509 connected to a shield 511. The shield 511 preferably is configured to prevent the tissue-piercing device 504 from piercing other tissue after the tissue-piercing device 504 has pierced the segments of torn soft tissue and guided the implant material 552 into the receiver 501.

FIGS. 28 and 28A illustrate another exemplary embodiment of the present invention. This embodiment is similar to that of FIGS. 27–27C. However, whereas the receiving portion 505 of FIGS. 27–27C includes a selectively manipulable plurality of elements 505a–b, the receiving portion 605, as illustrated in FIGS. 28–28A, preferably includes a plurality of elements 605a–b which are flexible and are biased toward an orientation in which the elements 605a and 605b form an opening or space 607. The flexibility of the plurality of elements 605a–b enables the elements 605a and 605b to be spread apart or separated as a length of implant material 652 is guided through the opening 607. Further, the bias of the elements 605a and 605b enables the elements 605a and 605b to return to their original, closed orientation after the tissue-piercing device 604 affixed to an implant 652 has passed into the opening 609, thereby grasping and retaining the tissue-piercing device 604 affixed to an implant 652 within the opening 607. The receiver 601 preferably is configured as a fork having two elements or tines 605a and 605b that preferably move apart slightly when the tissue-piercing device 604 forcibly passes between them using introducer tube 612. In this embodiment, introducer tube 612 preferably is modified such that the distal end of the introducer tube 612 preferably is blunt, rather than conical or chamfered as described above. The elements 605a and 605b are suitably configured to grasp or grip the tissue-piercing device 604. Preferably, a space or opening 607 is formed between the elements 605a–b, which is of suitable length, width, and shape to facilitate grasping and retaining the tissue-piercing device 604 within the space or opening 607. Preferably, once the tissue-piercing device 604 has been suitably grasped and retained within the space or opening 607, the guide structure 602 is selectively oriented and retracted as described more fully above.

In another embodiment, as illustrated in FIG. 28B, the tissue-piercing device 604 preferably is fixed or swedged to the length of implant material. In this embodiment, the guide structure 602 preferably comprises support device 603 which further includes a support member 609 connected to a shield 611. The shield 611 preferably is configured to prevent the tissue-piercing device 604 from piercing other body tissue after the tissue-piercing device 604 has pierced the segments of torn soft tissue and guided the implant material 652 into the receiver 601.

Depending upon the nature or location of the port of entry into the body or the structure of the soft tissue to be repaired, it may be necessary to deliver the suture or implant material in a particular orientation, such as a vertical, horizontal, or diagonal orientation, with respect to the instrument. Various embodiments of the present invention as described herein provide a method for repairing soft tissue by delivering a vertical stitch through that tissue. Various other embodiments of the invention provide for delivering and implanting only one leg of the suture or implant material within the soft tissue, as exemplified in FIG. 13. Alternative embodiments of the present invention, as described hereinafter with reference to FIGS. 29, 30, and 30A, provide a method for selectively orienting and implanting a plurality of legs or portions of the suture or implant material within soft tissue.

FIG. 29 represents an exemplary embodiment of the present invention which is capable of delivering a vertically oriented stitch or length of implant material within the soft tissue. In this embodiment, the guide structure 702 preferably includes a guide tube 708, a receiver tube 716 adjacent the guide tube 708, and a channel device 701 connected to a support member 703. Preferably, the guide tube 708 and receiver tube 716 are suitably spaced apart from the channel device 701 so that soft tissue in which an implant is being inserted can be disposed between the channel device 701 and the adjacent guide tube 708 and receiver tube 716. The channel device 701 is suitably configured to receive a length of implant material (not shown) extending through the guide tube 708 and through segments of torn tissue and is further configured to guide the length of implant material back through the soft tissue and toward the receiver tube 716. The guide tube 708 and receiver tube 716 are each suitably configured to allow a tissue-piercing device (not shown) and an introducer tube (not shown) to be delivered through the soft tissue to the distal ends 705a–b of the channel device 701. As shown, the tubes 708 and 716, respectively, preferably are oriented in a sagittal fashion. Preferably, as described above with reference to the embodiment of FIG. 1, the needles or tissue-piercing devices are retracted, and the introducer tubes remain connected to the distal ends 705a–b of the channel device 701. Thus, a path or passageway is created through which a suture or suture-like material preferably is guided and passed from guide tube 708, through the segments of tissue 748 and 746, through the channel device 701, and then into receiver tube 716. After the suture or implant material is suitably guided through the soft tissue and then into the receiver tube 716, the guide structure 702 preferably is selectively oriented and retracted, as described above, installing or delivering a vertical stitch in the soft tissue with both legs of the implant material contained within that tissue.

In another embodiment, as better seen in FIGS. 30 and 30A, the guide structure 802 preferably is suitably configured to orient the channel device 801 and the tubes 808 and 816 in a manner which delivers a horizontal stitch through the soft tissue. FIG. 30A illustrates the guide structure 802 and the meniscus from a superior vantage point. In this embodiment, the guide tubes 808 and 816 preferably are oriented in a transverse fashion. The channel device 801 preferably also is oriented in a transverse fashion. When the introducer tubes (not shown) contact the channel device 801, a path or passageway is created through which a suture or suture-like material preferably is passed from one guide tube 808 to the channel device 801 and then to another guide tube 816. Preferably, the guide structure 802 then is selectively oriented and retracted, and a horizontal stitch is installed in the soft tissue with both legs of the implant material contained within that tissue.

FIG. 32 is a diagrammatic depiction of a lateral view of the knee which illustrates an exemplary method of using the embodiment of the present device shown in FIG. 1 to repair the meniscus. It should be understood that this diagram is illustrative only and merely demonstrates one method of using one embodiment of the present invention. It should be noted further that FIG. 32 is not drawn to scale. In the illustrated example, a longitudinal tear in the meniscus, which is the cartilaginous tissue located between the femur and the tibia, of a left knee is being repaired. Arthroscopic repair of the meniscus requires no less than two incisions made in the anterior aspect of the knee. One of these required incisions, often referred to as the "working portal", is employed to insert various surgical instruments into the joint to perform the procedure. The other required incision, frequently referred to as the "scope portal", is used to insert the arthroscope. A third incision may be made, at the surgeon's discretion, to enable the delivery of fluid into the joint to distend and thereby enlarge the articular space in which the procedure is performed. As depicted in FIG. 32, the inventive device of FIG. 1 is inserted through the working portal and placed in the joint space with the distal, hook-shaped end placed over the posterior horn of the meniscus. In this case, the device is used to install a vertical stitch in the meniscus with an implant passing from one guide tube 116, through the meniscal tissue, and then into a second guide tube 108. The arthroscope inserted into the scope portal is used to view this repair and to project images of the surgical site onto a monitor located within the surgeon's view. After the device passes a stitch through the meniscal tissue, the device is selectively oriented, preferably by rotating the device 90 degrees, and then retracted from the surgical site so that the suture or implant legs may be joined by the surgeon through the working portal to facilitate fusion and healing of the meniscus. In accordance with the invention, selective orientation of the device is designed to enable friction between the implant and the meniscus to hold the implant in place and to enable the implant to disengage from the device as the device is withdrawn from the meniscus and toward the portal. Thus, as the device disengages from the surgical site, the legs of the implant pass through the gap between the guide tubes and are located in proximity with each other. However, it should be understood that while rotating the device 90 degrees is particularly well suited to the repair of meniscal tissue, the device of the present invention can be selectively oriented in any suitable manner, depending upon the location of the surgical site and the particular tissue that is being repaired or reattached.

As those skilled in the art will appreciate, based upon the above description, the principles of the present invention are equally applicable to the delivery of a diagonal stitch through the segments of torn tissue. The guide tube, receiver tube, and channel device can be suitably configured and oriented in a diagonal manner, and a diagonal stitch therefore can be delivered and installed through the soft tissue with both legs of the implant material contained within that tissue.

The device of the instant invention can be either reusable or disposable. The components of the present invention, such as the tissue-piercing device(s), guide tube(s), introducer tube(s), and receiver tube(s), are preferably made of stainless steel, though in some cases titanium or Nitonol will serve better where multiple or severe angles or bends are required in the guide structure. The handles and the implant drive wheels can be made of either metal or medical grade plastics. In some cases, where the force required to drive the guide structure through tissue is sufficiently low, the guide tube(s), introducer tube(s), and receiver tube(s) can be made of medical grade plastic to allow for greater flexibility.

While the invention has been particularly shown and described with reference to exemplary embodiments, it will be understood by those skilled in the art that various changes in form and detail may be made without departing from the spirit and the scope of the present invention.

What is claimed is:

1. Apparatus for use in installing an implant in soft tissue, comprising a guide structure insertable through a body portal and into proximity with the soft tissue, the guide structure being configured to guide a length of the implant through the soft tissue and to bring legs of the length of implant into proximity with each other, the guide structure being further configured to be withdrawn toward the body portal in a manner which (a) causes the guide structure to become disengaged from the length of implant, and (b) leaves the length of implant extending through the soft tissue and the legs of the length of implant in proximity with each other, wherein the guide structure includes (a) a pair of guide portions supported in spaced apart relation to each other and defining a gap which enables soft tissue to be disposed between the guide portions, (b) a tissue piercing device moveable in the gap between the guide portions and configured to pierce soft tissue disposed in the gap between the guide portions, and (c) an introducer tube configured to receive and guide the length of implant, the introducer tube being moveable in opposite directions in the gap between the guide portions, the introducer tube being moveable in one direction to form a passageway in the gap for guiding the length of implant through soft tissue in the gap and in an opposite direction for reestablishing the gap between the guide portions, the guide portions being configured to guide the legs of the length of implant into proximity with each other, and the re-established gap between the guide portions enabling legs of the length of implant to pass therethrough as the guide structure is being withdrawn toward the body portal; and a force applying device including a drive wheel extending at least partially into the introducer tube, the drive wheel being rotatable about an axis and having an external surface configured for applying force to the length of implant disposed in the introducer tube to move the length of implant in the introducer tube.

2. Apparatus as defined in claim 1, wherein the force applying device is selectively engageable with the length of implant to drive the length of implant in the guide structure and selectively disengageable from the length of implant to enable the length of implant to slide in the guide structure.

3. Apparatus as defined in claim 2, wherein the guide structure is configured to be at least partially located within an articular space in order to install an implant in soft tissue located within the articular space.

4. Apparatus as defined in claim 2, wherein the guide structure is configured to be at least partially located within a knee to install an implant in the meniscus in the knee.

5. Apparatus as defined in claim 4, wherein the pair of guide portions comprises a pair of guide tubes, each of which is disposed in a common plane which has a thickness equal to the largest outer diameter of the pair of guide tubes, the gap being located in the common plane, the introducer tube being moveable in the common plane and configured to guide the length of implant in the common plane, the tissue piercing device being moveable in the common plane, and a thickness of the common plane being further dimensioned to enable the pair of guide tubes to be at least partially located within an articulated joint.

6. Apparatus as defined in claim 1, wherein the tissue piercing device is formed at a distal end of a shaft which is slideable in opposite directions in the introducer tube, the shaft enabling the tissue piercing device to be moveable in one direction in the gap between the guide portions to pierce soft tissue and in an opposite direction for withdrawing the tissue piercing device from the introducer tube, so that a length of implant can be inserted in and is moveable in the introducer tube.

7. Apparatus as defined in claim 6, wherein a handle is fixed to a proximal end of the shaft.

8. Apparatus as defined in claim 6, wherein the introducer includes a distal end portion located to follow the tissue piercing device through soft tissue and to extend at least partially into one of the pair of guide tubes to form the passageway.

9. Apparatus as defined in claim 8, wherein the guide tubes are fixed to each other, and the introducer tube is moveable in at least one of the guide tubes.

10. Apparatus as defined in claim 1, wherein at least one of the pair of guide portions has a bend configured to enable the at least one of the pair of guide portions to extend about anatomical structures.

11. Apparatus as defined in claim 10, wherein the pair of guide portions comprises a pair of guide tubes, and the introducer tube is moveable within the at least one of the pair of guide tubes, the introducer tube having a flexibility that enables the introducer tube to move lengthwise in the at least one of the pair of guide tubes despite the bend.

12. Apparatus as defined in claim 1, wherein the drive wheel is selectively moveable in one direction transverse to the length of implant to engage and drive the length of implant, and in an opposite direction to disengage from the length of implant to allow the length of implant to slide within the introducer tube.

13. Apparatus as defined in claim 12, wherein the force applying device further comprises a second wheel rotatable about an axis parallel to the axis of the drive wheel, the second wheel having an outer surface engaging the drive wheel in a manner which rotates the drive wheel in the opposite direction as the second wheel, thereby enabling forces to be applied to the second wheel in the same direction in which the length of implant is intended to be moved.

14. Apparatus as defined in claim 1, wherein the force applying device further comprises a second wheel rotatable about an axis parallel to the axis of said drive wheel, the second wheel having an outer surface engaging the drive wheel in a manner which rotates the drive wheel in the opposite direction as the second wheel, thereby enabling forces to be applied to the second wheel in the same directions in which the length of implant is intended to be moved.

15. Apparatus as defined in claim 1, wherein the pair of guide portions comprises a pair of guide tube sets, each of which comprises a pair of adjacent guide tubes, the pair of guide tube sets configured to enable portions of the length of implant to be guided through soft tissue, and at least one pair of adjacent guide tubes being further configured to maintain legs of the portions of implant in adjacent spaced relation to each other as the portions of implant are guided through soft tissue.

16. Apparatus as defined in claim 15, wherein at least one pair of adjacent guide tubes comprises a single lumen tube structure defining a pair of tube portions and a reduced central portion joining the pair of tube portions, each of the pair of tube portions configured to guide a portion of the length of implant in a lengthwise direction, and the central portion configured to maintain said pair of tube portions in spaced relation to each other and allowing a connecting portion of the length of implant to slide sideways in the central portion with an interference fit.

17. Apparatus as defined in claim 1, wherein at least one of a pair of guide portions comprises a single lumen tube structure defining a pair of tube portions and a reduced central portion joining the pair of tube portions, each of the pair of tube portions configured to guide a portion of the length of implant in a lengthwise direction, and the central portion configured to maintain the pair of tube portions in spaced relation to each other and allowing a connecting portion of the length of implant to slide sideways in the central portion with an interference fit.

18. Apparatus as defined in claim 1, wherein the guide structure comprises a guide tube and a receiver connected with the guide tube.

19. Apparatus as defined in claim 18, wherein the receiver comprises a plurality of elements configured to form an opening for receiving and retaining the length of implant guided through torn tissue.

20. Apparatus as defined in claim 19, wherein the plurality of elements are moveable relative to each other to form the opening, the guide structure further comprising a manipulator for selectively moving the plurality of elements relative to each other to form the opening.

21. Apparatus as defined in claim 19, wherein the plurality of elements are flexible and are biased toward an orientation in which the elements form the opening, the flexibility of the elements enabling the elements to be spread apart as the length of implant is guided through the opening, and the bias of the elements enabling the elements to return to the orientation after the length of implant is in the opening, thereby retaining the length of implant in the opening.

22. Apparatus as defined in claim 19, wherein the plurality of elements are flexible and are biased toward an orientation in which the elements form the opening, the flexibility of the elements enabling the elements to spread apart as a tissue-piercing device connected to the length of implant is guided through the opening, and the bias of the elements enabling the elements to return to the orientation after the tissue-piercing device is in the opening, thereby retaining the tissue-piercing device in the opening.

23. Apparatus as defined in claim 22, wherein the tissue-piercing device is fixed to the length of implant, and wherein a shield is connected to the guide structure, the shield configured to prevent the tissue piercing structure from piercing other body tissue after the tissue-piercing device has pierced soft tissue and guided the implant into the receiver.

24. Apparatus as defined in claim 20, wherein a tissue-piercing device is fixed to the length of implant, and wherein a shield is connected to the guide structure, the shield configured to prevent the tissue-piercing device from piercing other body tissue after the tissue-piercing device has pierced soft tissue and guided the implant into the receiver.

25. Apparatus as defined in claim 1, wherein the guide structure comprises adjacent guide and receiver tubes and a channel device connected to a support member, the adjacent guide and receiver tubes being spaced from the channel device so that soft tissue in which an implant is being inserted can be disposed between the adjacent guide and receiver tubes and the channel, the channel device being configured to (i) receive the length of implant extending through the guide tube and through soft tissue and (ii) guide the length of implant back through the soft tissue and toward the receiver tube.

26. A method for installing an implant in soft tissue, comprising
providing a guide structure as set forth in claim 1,
locating the guide structure in a selected orientation with respect to the soft tissue,
operating the guide structure to guide a length of implant through the soft tissue, and
withdrawing the guide structure from the soft tissue in a manner which maintains the implant in the soft tissue and disengages the guide structure from the length of implant with legs of the length of implant in proximity to each other.

27. The method as defined in claim 26, further comprising
manipulating the guide structure into a selected orientation after the length of implant has been guided through the soft tissue, the selected orientation enabling friction between the length of implant and the soft tissue to cause the guide structure to disengage from the length of implant as the guide structure withdrawn from the soft tissue.

28. A method for installing an implant in soft tissue within an articular space, comprising
providing a guide structure as defined in claim 1,
locating the guide structure in a first selected orientation relative to soft tissue in the articular space,
operating the guide structure to guide a length of implant through the soft tissue in the articular space, and
manipulating the guide structure into a second selected orientation after the length of implant has been guided through the soft tissue, the second selected orientation enabling friction between the length of implant and the soft tissue to cause the guide structure to disengage from the length of implant as the guide structure is withdrawn from the soft tissue.

29. A method as defined in claim 28, wherein the articular space comprises a knee joint repair space and the soft tissue comprises a meniscus.

30. Apparatus for use in installing an implant in soft tissue, comprising
a guide structure insertable through a body portal and into proximity with the soft tissue, the guide structure being configured to guide a length of the implant through the soft tissue and to bring legs of the length of implant into proximity with each other, the guide structure being further configured to be withdrawn toward the body portal in a manner which (a) causes the guide structure to become disengaged from the length of implant, and (b) leaves the length of implant extending through the soft tissue and the legs of the length of implant in proximity with each other,
wherein the guide structure includes (a) a pair of guide portions supported in spaced apart relation to each other and defining a gap which enables soft tissue to be disposed between the guide portions, (b) a tissue piercing device moveable in the gap between the guide portions and configured to pierce soft tissue disposed in the gap between the guide portions, and (c) an introducer moveable in opposite directions in the gap between the guide portions, the introducer being moveable in one direction to form a passageway in the gap for guiding the length of implant through soft tissue in the gap and in an opposite direction for reestablishing the gap between the guide portions; the guide portions being configured to guide the legs of the length of implant into proximity with each other, the pair of guide portions including a pair of guide tube sets, each of which includes a pair of adjacent guide tubes, the pair of guide tube sets configured to enable portions of the length of implant to be guided through soft tissue, and at least one pair of adjacent guide tubes being further configured to maintain legs of the portions of implant in adjacent spaced relation to each other as the portions of implant are guided through soft tissue; and the re-established gap between the guide portions enabling legs of the length of implant to pass therethrough as the guide structure is being withdrawn toward the body portal.

31. Apparatus as defined in claim 30, wherein at least one pair of adjacent guide tubes comprises a single lumen tube structure defining a pair of tube portions and a reduced central portion joining the pair of tube portions, each of the pair of tube portions configured to guide a portion of the length of implant in a lengthwise direction, and the central portion configured to maintain said pair of tube portions in spaced relation to each other and allowing a connecting portion of the length of implant to slide sideways in the central portion with an interference fit.

32. Apparatus for use in installing an implant in soft tissue, comprising
a guide structure insertable through a body portal and into proximity with the soft tissue, the guide structure being configured to guide a length of the implant through the soft tissue and to bring legs of the length of implant into proximity with each other, the guide structure being further configured to be withdrawn toward the body portal in a manner which (a) causes the guide structure to become disengaged from the length of implant, and (b) leaves the length of implant extending through the soft tissue and the legs of the length of implant in proximity with each other,
wherein the guide structure includes (a) a pair of guide portions supported in spaced apart relation to each other and defining a gap which enables soft tissue to be disposed between the guide portions, (b) a tissue piercing device moveable in the gap between the guide portions and configured to pierce soft tissue disposed in the gap between the guide portions, and (c) an introducer moveable in opposite directions in the gap between the guide portions, the introducer tube moveable in one direction to form a passageway in the gap for guiding the length of implant through soft tissue in the gap and in an opposite direction for reestablishing the gap between the guide portions; the guide portions being configured to guide the legs of the length of implant into proximity with each other, at least one of a pair of guide portions including a single lumen tube structure defining a pair of tube portions and a reduced central portion joining the pair of tube portions, each of the pair of tube portions configured to guide a portion of the length of implant in a lengthwise direction, and the central portion configured to maintain the pair of tube portions in spaced relation to each other and allowing a connecting portion of the length of implant to slide sideways in the central portion with an interference fit; and the re-established gap between the guide portions enabling legs of the length of implant to pass therethrough as the guide structure is being withdrawn toward the body portal.

33. Apparatus for use in installing an implant in soft tissue, comprising a guide structure insertable through a body portal and into proximity with the soft tissue, the guide structure being configured to guide a length of the implant through the soft tissue and to bring legs of the length of implant into proximity with each other, the guide structure being further configured to be withdrawn toward the body portal in a manner which (a) causes the guide structure to become disengaged from the length of implant, and (b) leaves the length of implant extending through the soft tissue and the legs of the length of implant in proximity with each other, wherein the guide structure includes a guide tube and a receiver connected with the guide tube, the receiver including a plurality of elements configured to form an opening for receiving and retaining the length of implant guided through torn tissue.

34. Apparatus as defined in claim 33, wherein the plurality of elements are moveable relative to each other to form the opening, the guide structure further includes a manipulator for selectively moving the plurality of elements relative to each other to form the opening.

35. Apparatus as defined in claim 33, wherein the plurality of elements are flexible and are biased toward an orientation in which the elements form the opening, the flexibility of the elements enabling the elements to be spread apart as the length of implant is guided through the opening, and the bias of the elements enabling the elements to return to the orientation after the length of implant is in the opening, thereby retaining the length of implant in the opening.

36. Apparatus as defined in claim 33, wherein the plurality of elements are flexible and are biased toward an orientation in which the elements form the opening, the flexibility of the elements enabling the elements to spread apart as a tissue-piercing device connected to the length of implant is guided through the opening, and the bias of the elements enabling the elements to return to the orientation after the tissue-piercing device is in the opening, thereby retaining the tissue-piercing device in the opening.

37. Apparatus as defined in claim 36, wherein the tissue-piercing device is fixed to the length of implant, and wherein a shield is connected to the guide structure, the shield configured to prevent the tissue piercing structure from piercing other body tissue after the tissue-piercing device has pierced soft tissue and guided the implant into the receiver.

38. Apparatus as defined in claim 34, wherein a tissue-piercing device is fixed to the length of implant, and wherein a shield is connected to the guide structure, the shield configured to prevent the tissue-piercing device from piercing other body tissue after the tissue-piercing device has pierced soft tissue and guided the implant into the receiver.

* * * * *

UNITED STATES PATENT AND TRADEMARK OFFICE
CERTIFICATE OF CORRECTION

PATENT NO.    : 6,443,963 B1
DATED         : September 3, 2002
INVENTOR(S)   : Jeffrey P. Baldwin et al.

It is certified that error appears in the above-identified patent and that said Letters Patent is hereby corrected as shown below:

<u>Title page,</u>
Item [56], U.S. PATENT DOCUMENTS, replace "5,442,472" with -- 5,443,472 --.

<u>Column 11,</u>
Line 8, replace "tot eh" with -- to the --.

Signed and Sealed this

Thirty-first Day of December, 2002

JAMES E. ROGAN
*Director of the United States Patent and Trademark Office*